United States Patent [19]

Tajima

[11] Patent Number: 4,595,657
[45] Date of Patent: Jun. 17, 1986

[54] PROCESS FOR PREPARING AN INHIBITING AGENT AGAINST PROLIFERATION OF ANIMALS MALIGNANT TUMOR CELLS

[75] Inventor: Tomoyuki Tajima, Ichikawa, Japan

[73] Assignees: Koken Ltd., Tokyo; Youichiro Nagasu, Kanagawa, both of Japan

[21] Appl. No.: 583,011

[22] Filed: Feb. 23, 1984

[30] Foreign Application Priority Data

May 6, 1983 [JP] Japan ................................. 58-78300

[51] Int. Cl.$^4$ ........................... C12P 1/00; C12P 21/00
[52] U.S. Cl. ....................................... 435/41; 435/68; 435/240
[58] Field of Search .................... 435/240, 241, 68, 41

[56] References Cited

U.S. PATENT DOCUMENTS 4,415,553 11/1983 Zhabilov et al. .................... 435/68

OTHER PUBLICATIONS

Matsuda et al., Chem. Abst. vol. 92 (1980), p. 20255q.

*Primary Examiner*—Sam Rosen
*Attorney, Agent, or Firm*—Lowe Price Leblanc Becker & Shur

[57] ABSTRACT

The present invention relates to a process for preparing an inhibiting agent against the proliferation of malignant tumor cells of animals including human beings by cultivating animal malignant tumor cells, removing said malignant tumor cells from the culture medium and successively isolating a fraction having a molecular weight not less than 500 by fractional filtration.

2 Claims, No Drawings

PROCESS FOR PREPARING AN INHIBITING AGENT AGAINST PROLIFERATION OF ANIMALS MALIGNANT TUMOR CELLS

SUMMARY OF THE INVENTION

The present invention relates to a process for preparation of an inhibiting agent against the proliferation of malignant tumor cells of animals including human beings.

The substance, which is obtained by cultivating animal malignant tumor cells on a medium and extracting the medium after removing said tumor cells, shows a remarkable inhibiting activity against the proliferation of the malignant tumor cells, although it shows the inhibiting activity somewhat against the proliferation to normal cells, too.

The fractions are prepared by cultivating the malignant tumor cells in the culture medium for extraction (extraction medium) at a temperature between 30° C. and 37° C., removing said malignant tumor cells, and subjecting the culture medium to filtration by molecular sieving to fractionate at the molecular weight of 500. For example, the culture medium is filtered through a membrane filter which fractionates at the molecular weight of 500, such as a UM 05 filter or YA 05 filter made by Amicon, such that the culture medium is separated into a fraction having a molecular weight not less than 500 and another fractions having a molecular weight less than 500. When these inhibiting effects against the proliferation of the cultivated tumor cells were investigated by using each of these fractions, it was determined that the substance isolated from the fraction having a molecular weight not less than 500 showed more remarkable inhibiting activity than the inhibiting activity of the filtrate having a molecular weight less than 500. A high inhibiting activity against proliferation was shown even when the fraction was diluted and the effective ingredient, the fraction having a molecular weight not less than 500, was more concentrated than the fraction having the molecular weight less than 500.

Further, it was determined that the inhibiting agent against the proliferation of malignant tumor cells obtained by this method hardly showed such side effects as the conventional antineoplastic agent showed.

The present invention is to provide a process for preparing an inhibiting agent against the proliferation of animal malignant tumor cells, for instance, firstly by transplanting the malignant tumor cells incubated in the culture medium for growth (growth media) into another culture medium for extraction (extraction media), cultivating said incubated cells in the extraction medium, subjecting the extraction medium to ultrafiltration by passing the medium through an ultrafiltration membrane capable of fractionating at a molecular weight of 500 and isolating the fraction having a molecular weight not less than 500.

EXAMPLE:

(1) Cells used as experimental materials: Established cells HRC originated from human renal carcinoma cells.
(2) Culture medium for extraction culture: Basal Medium Eagle (BME) for diploid supplemented with 10% new born calf serum,
(3) Cultivation method: More than $2 \times 10^7$ cells of established cells HRC originated from human renal carcinoma cells were placed with 50 ml of BME in a culture bottle, the bottom area of which was 150 $cm^2$ and were cultivated for one week. After that, the culture medium was subjected to ultrafiltration by passing the medium through an ultrafiltration membrane capable of fractionating at a molecular weight of 500, for instance, an UM 05 filter or YA 05 filter made by Amicon. The filtered medium was then separated into a fraction having a molecular weight not less than 500 and a fractional substance having a molecular weight less than 500 and isolating each of the fractions.

Secondly, the experiments to confirm the effect of the present invention are as follows:
(1) Assay method for an inhibiting agent against the proliferation of malignant tumor cells.

$10^4$ Cells of established cells HRC originated from human renal carcinoma cells were inoculated in a plastic dish 15 mm in diameter and were cultivated in BME supplemented with 10% bovine serum for 24 weeks. Second, the fraction having a molecular weight not less than 500 was designated fraction 1, and another fractional substance having a molecular weight less than 500 was designated fraction 2 and to each of the culture media of these fractions, amino acids, vitamins and glucose were added in the same amount as the first culture media BME. Replacement of the culture medium, which had been incubated for 24 weeks was made and the culture media containing these isolated substances, were then incubated with established HRC cells at 37° C. under the conditions of 5% $CO_2$ and 100% humidity for six days and the proliferation of established cells HRC originated from human renal carcinoma cells were then studied.

(2) Experimental results.

The table shows the inhibition rate against the proliferation of malignant tumor cells. The proliferation-inhibiting figures were calculated by subtracting each of the survival numbers from the numbers of added human renal carcinoma cells HRC. The proliferation-inhibiting figure shown by the culture medium containing a substance obtained from the fraction having a molecular weight less than 500 and the proliferation-inhibiting figure shown by the culture medium containing a substance obtained without conducting the filtration by molecular sieving were calculated in percentage (%) per the proliferation-inhibiting figure shown by the culture medium containing a fraction having the molecular weight not less than 500.

As the results, a remarkable proliferation-inhibiting effect was observed in fr. 1 having the molecular weight not less than 500 and an efficient proliferation-inhibiting effect was observed also when the fraction was diluted. The reproductivity was confirmed because it could be shown that the effective ingredient was much more concentrated than other groups and common results were obtained between the two lots.

TABLE

| Lot Nos. | Fraction | Proliferation-inhibiting rates | |
|---|---|---|---|
| | | Diluted × 1 | Diluted × 2 |
| 830112 | Whole | 82% | 28% |
| | fr. 1 | 100% | 94% |
| | fr. 2 | 32% | 6% |
| 74-1 | Whole | 62% | 11% |
| | | 100% | 97% |
| | | 14% | 0% |

What we claim is:

1. A process for preparing an inhibiting agent against the proliferation of human renal carcinoma cells comprising cultivating human renal carcinoma cells from said culture medium, and successively isolating a fraction from the culture medium having a molecular weight not less than 500 by fractional filtration, said fraction inhibiting the proliferation of human renal carcinoma cells.

2. A process for preparing an inhibiting agent against the proliferation of human renal carcinoma cells according to claim 1, wherein the culture medium is Basal Medium Eagle not containing serum.

* * * * *